United States Patent [19]

Kurland

[11] Patent Number: 5,139,981
[45] Date of Patent: Aug. 18, 1992

[54] PROCESS FOR PREPARING SILVER(I)-EXCHANGED RESINS

[75] Inventor: Jonathan J. Kurland, Charleston, W. Va.

[73] Assignee: Union Carbide Chemicals & Plastics Technology Corporation, Danbury, Conn.

[21] Appl. No.: 721,310

[22] Filed: Jun. 26, 1991

Related U.S. Application Data

[63] Continuation of Ser. No. 552,327, Jul. 13, 1990, abandoned, which is a continuation of Ser. No. 65,755, Jun. 24, 1987, abandoned.

[51] Int. Cl.$^5$ .................. B01J 37/30; B01J 20/26; B01D 15/04; C07C 51/42
[52] U.S. Cl. .................. 502/11; 210/683; 210/690; 252/184; 502/402; 521/33; 562/608
[58] Field of Search .................. 502/11, 402, 159; 210/683, 690; 252/184; 521/26, 31, 33

[56] References Cited

U.S. PATENT DOCUMENTS 4,615,806 10/1986 Hilton .................. 210/690

FOREIGN PATENT DOCUMENTS 0196173 10/1986 European Pat. Off. .
3329781 2/1985 Fed. Rep. of Germany .
2112394 7/1983 United Kingdom .

OTHER PUBLICATIONS

Pohl & Johnson, "Ion Chromotography—The State of the Art", 18, *J. Chromat. Sci.*, pp. 442-452 (1980).
Hingorani & Venkateswarlu, "Removal of Radioactive Iodine and Methyl Iodide by Use of Silver-Impregnated Resin", 12, *Chem Eng. World*, pp. 59-60 (1977).
Johnson & Stevenson, *Basic Liquid Chromatography*, "Chapter V. Ion Exchange" pp. 116-125, 146 and 147 (1978).
Kornblum, Jones & Anderson, "A New and Selective Method of Oxidation. The Conversion of Alkylhalides and Alkyl Tosylates to Aldehydes" 75, *J. Amer. Chem. Soc.* pp. 4113-4114 (1959).
Pitochelli, "Ionic Exchange Catalysis and Matrix Effects" (A compendium reprinted by Rohm and Haas in Jun. 1980) pp. 1-4, 8 and 19.

*Primary Examiner*—Paul E. Konopka
*Attorney, Agent, or Firm*—Reynold J. Finnegan

[57] ABSTRACT

This invention relates to a method for removing halides from liquid carboxylic acid contaminated with a halide impurity by contacting the liquid halide-contaminated acid with a silver(I)-exchanged macroreticular resin. The halide reacts with the resin-bound silver and is removed from the carboxylic acid stream. The present invention also relates to an improved method for producing silver-exchanged macroreticular resins suitable for use in the present invention.

13 Claims, 1 Drawing Sheet

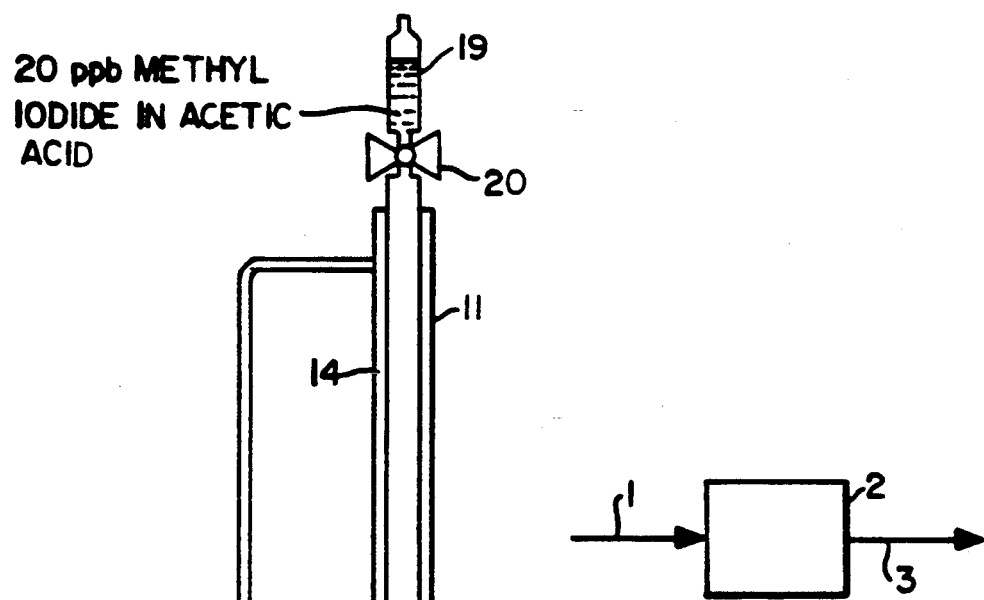
F I G. 1
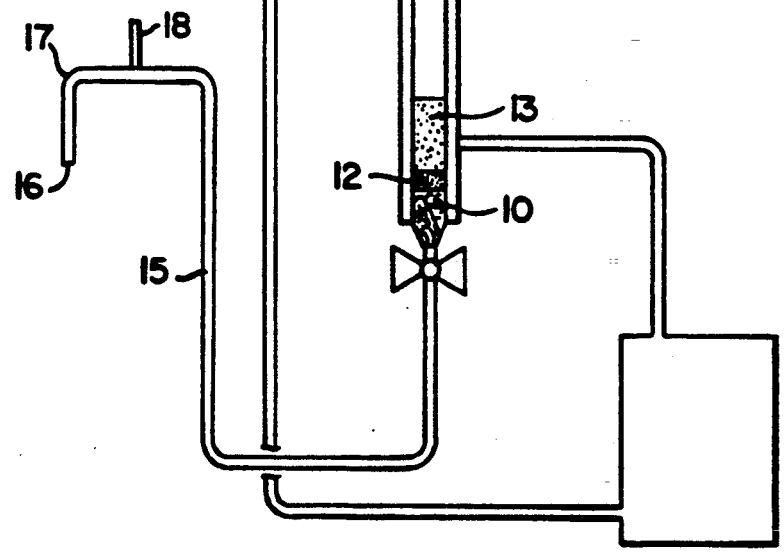
F I G. 2

PROCESS FOR PREPARING SILVER(I)-EXCHANGED RESINS

This application is a continuation of prior U.S. application Ser. No. 552,327, filed Jul. 13, 1990, which is a continuation of application Ser. No. 065,755, filed Jun. 24, 1987, both applications now abandoned.

BACKGROUND OF THE INVENTION

1. Field of the Invention

The subject invention relates to a method of removing halides from carboxylic acids to produce essentially halide-free carboxylic acid. The invention also relates to a method of preparing both gelular and macroreticular silver(I)-exchanged resins.

2. Description of Related Art

Commercial production of unsaturated esters is carried out by catalytically reacting the corresponding carboxylic acid with an alkene and oxygen in the presence of a noble metal catalyst. For example, vinyl acetate is produced by reaction of acetic acid with ethylene in the presence of the noble metal catalyst and oxygen. To avoid premature deactivation and maximize the life of the noble metal esterification catalyst, it is desirable that the reactants be essentially free of halides, particularly iodides.

While the alkene reactant is essentially halide-free, halides may be introduced into the esterification reactor with the carboxylic acid. For example, in one commercially accepted procedure for making carboxylic acids, an alcohol such as methanol is carbonylated in the presence of a halide-promoted rhodium catalyst to produce a carboxylic acid such as acetic acid. Typically, the halide promoter is a bromide or an iodide. It is not unusual, therefore, for a small amount of the halide promoter or a derivative thereof to be recovered with the acetic acid prepared in the fashion. Unless removed by treatment, the halide accompanies the acid into the oxidative esterification reactor.

Unfortunately, the concentration of halide in the carboxylic acid can be very low and still unacceptably shorten the life of the esterification catalyst. For example, one part per billion (ppb) of iodide has a deleterious effect, substantially shortening the useful life of the noble metal esterification catalyst used in preparing vinyl acetate. Therefore, iodide removal must be essentially quantitative to be effective in prolonging catalyst life.

Pohl and Johnson ("Ion Chromatography—The State-Of-The-Art," 18 J. Chromat. Sci. 442 (1980)) describe using silver(I)-exchanged resin as a suppressor in anion ion chromatography to modify the chromatographic eluent and achieve a sensitive detection of weakly electrolytic ionic species. The resin is used to remove high concentrations of interfering halides (e.g., brines) from the eluent. Microporous rather than macroporous exchange resins are preferred as suppressors because macroporous resins strongly absorb weak electrolytes.

Hingorani and Venkateswarlu ("Removal Of Radioactive Iodine and Methyl Iodide by use of Silver-impregnated Resin," 12 Chem. Eng. World 59 (1977)) disclose a method of batchwise removal of radioactive iodine and labelled methyl iodide from aqueous solutions using a silver-impregnated gelular resin. The aqueous solutions were intended merely as an expedient during experimentation directed toward removal of iodine and methyl iodide from waste streams obtained from plants which reprocess irradiated fuel elements. This method is unsatisfactory for removing iodide from carboxylic acids used to produce commercial quantities of vinyl carboxylates. First, the method proceeds at a slow rate. Even after more than 110 hours, only about 83% of the iodide in the solution was absorbed—96% removal requires about 150 hours of treatment. Hingorani et al suggest that the absorption rate is low in their process because methyl iodide is not easily hydrolyzed in aqueous solution. Also, continuous processes are preferred to batch techniques for commercial use because batch techniques require extremely large vessels, catalyst charges, holding tanks, and the like. Thus, one skilled in the art would not consider this technique commercially practicable for treating carboxylic acids used to produce large quantities of unsaturated esters.

Preparation of a silver-substituted cation exchange resin as used by Hingorani also has heretofore been difficult and inefficient. A cation exchange resin typically is soaked overnight in a solution of silver nitrate ($AgNO_3$). The exchange of silver onto the resin produces nitric acid as a byproduct. Nitric acid is both a strong acid and a strong oxidant. As the exchange reaction progresses, the increasing activity due to the accumulating nitric acid causes the equilibrium exchange reaction to stop when about 5% of the silver still remains in solution. Further, the oxidizing power of the byproduct nitric acid requires that the exchange resin be washed thoroughly before use, to remove substantially all of the nitric acid.

Applicant has determined that cationic gelular resins, such as Amberlite® IR-120 used by Hingorani et al, are not suitable for removing halides from carboxylic acids because carboxylic acids cause such resins to shrink, making internal active sites inaccessible to reactants and increasing pressure drop in a fixed-bed system. To achieve reasonable reaction rates, relatively high temperatures, i.e., at least about 60° C., must be utilized. However, high temperature promote corrosion of equipment, releasing polyvalent metal ions into the carboxylic acid stream. Polyvalent metal ions are significant contributors to resin degradation.

It is an object of this invention to provide a method for essentially complete removal of halide impurities from carboxylic acid by contacting halide-containing acid with a silver-exchanged macroreticular resin.

It is a further object of this invention to provide an improved method for preparing macroreticular silver-exchanged resins suitable for use in the present invention.

SUMMARY OF THE INVENTION

In accordance with these and other objects, this invention relates to a method for removing halides from liquid carboxylic acid contaminated with a halide impurity which comprises contacting the liquid halid-contaminated acid with a silver(I)-exchanged macroreticular resin. The halide reacts with the resin-bound silver and is removed from the carboxylic acid stream. The present invention also relates to an improved method for producing silver-exchanged macroreticular resins suitable for use in the present invention.

BRIEF DESCRIPTION OF THE DRAWINGS

FIG. 1 is a schematic diagram of an embodiment of this invention.

FIG. 2 is a schematic diagram of an embodiment of an apparatus for using the resins of this invention.

DETAILED DESCRIPTION OF THE INVENTION

In a first aspect, the present invention pertains to a method for producing substantially halide-free carboxylic acid to be used to prepare unsaturated esters by reaction between the acid and an olefin in the presence of oxygen over a noble metal catalyst. The present invention is based on the discovery that halides can be essentially completely removed from carboxylic acids containing halide impurities by contacting the contaminated stream with a silver(I)-exchanged macroreticular resin. Generally, the halide contaminant in carboxylic acid will be in the form of an alkyl halide. For example, in preparing acetic acid by catalytic carbonylation of methanol, the acetic acid becomes contaminated primarily with methyl iodide. The method of this invention is especially useful for removing methyl iodide from acetic acid. However, the scope of the invention is not limited to this embodiment, and broadly includes removal of primary halides from carboxylic acids in general. In another aspect, the present invention pertains to an improved method for preparing silver(I)-exchanged resins including macroreticular resins, suitable for use in the present invention.

Any liquid carboxylic acid can be treated by the method of this invention. While there currently is no economic incentive to remove halides from formic acid, because formic acid decomposes over a noble metal catalyst and thus cannot be used to prepare an unsaturated ester by reaction with an olefin as outlined above, the presence in low amounts of formic acid in other carboxylic acids does not damage or deactivate the resin. Lower carbon number carboxylic acid homologs having between 2 and 5 carbon atoms, such as acetic, propionic, butyric, and valeric acids, are particularly suitable for treatment by the method of this invention.

Prior to contacting the acid with the resin, the carboxylic acid should be substantially free of contaminants which damage or deactivate the macroreticular resin. For examples, resins are susceptible to degradation by high concentrations of chemical oxidants, such as nitric acid, sulfuric acid, and perchloric acid. Therefore, care should be taken to minimize the concentration of such components in the reactant streams Also, corrosion products (polyvalent metal ions) from aluminum or steel used to construct the reaction circuit are a major contaminant source. Efforts to reduce corrosion are therefore important.

Contaminants which reduce silver ions on the resin to metallic silver also must be removed from the carboxylic acid before carrying out the method of this invention. Such reducing agents include formaldehyde. Not only is silver metal a less effective halide-removal agent, but also silver metal may be removed from the resin.

As used herein, "halide" includes both halogen ions and halogen-containing compounds. Preferably, the "halide" contaminants to be removed using the method of the present invention are limited to bromide and iodide ions and organic bromides and iodides such as alkyl bromides and alkyl iodides. Most preferably, the "halide" is limited to iodide ions and organic iodides. Less expensive methods are known for removing chloride and fluoride ions from carboxylic acids. For example, chloride and fluoride ions can effectively be removed using an anion-exchange guard bed. The large quantity of chloride contaminant which could be present as an impurity in the carboxylic acid feed, if, for example, a leak developed in a cooling unit which utilized salt water brine as the coolant, make it preferable that a guard bed be used in the method of halide removal described herein. Those skilled in the art recognize that halogen ion removal is essentially diffusion-limited, and that the reaction of a halogen ion with the silver(I) ions on the catalyst is essentially instantaneous and quantitative. However, reaction of a silver(I) ion with an organic halide to bind the halide to the silver requires that the organic and halide moieties be separated. The energy required to activate these moieties, also called the "activation energy," must be supplied or otherwise available before the silver(I) ion and the halogen ion can bond.

Those skilled in the art appreciate that this activation energy increases as the molecular weight of the halogen decreases and as the molecular weight of the organic moiety increases. However, the former effect is stronger than the latter, i.e., the difference in activation energies between methyl bromide and methyl iodide is larger than the difference in activation energies between methyl iodide and ethyl iodide. The activation energy is a function of the temperature of the system and the identity of the organic moiety. Therefore, it is not possible to state a broad rule of effectiveness of the silver-exchanged resin for removal of organic chloride and organic fluoride compounds.

While a 1 ppm-lever chloride contamination level in the carboxylic acid may not seriously affect the esterification catalyst, such a level greatly increases the rate of resin usage. In fact, even though chloride concentrations of less than 100 ppb in a carboxylic acid such as acetic acid cannot be detected, this chloride concentration in a carboxylic acid stream has a deleterious effect on the resin life. Therefore, economic considerations suggest that the chloride concentration in the feed to the silver(I)-exchanged resin preferably not exceed 100 ppb, more preferably not exceed 50 ppb, and most preferably not exceed 25 ppb. Such levels can be obtained by using an anion-exchange guard bed, as described above.

FIG. 1 schematically illustrates one embodiment of this invention. Halide contaminated carboxylic acid is introduced through inlet pipe 1 to vessel 2, which contains a fixed bed of a silver-exchanged resin. The contaminated acid stream contacts the resin in the vessel, and halides are removed by virtue of their reaction with silver on the resin. Halide-free acid is removed through outlet pipe 3. Those skilled in the art will recognize that a variety of other options also are available, e.g., a plurality of vessels can be served by a plurality of inlet and outlet pipes, as appropriate.

Applicant has discovered that macroreticular cation-exchange resins onto which silver(I) ($Ag^+$) is loaded by ion exchange are particularly suitable for removable of halides from carboxylic acids. Basically, suitable resins are discrete particles of polystyrene cross-linked with divinyl benzene. Macroreticular resins typically have a uniform pore structure. Resins having pore diameters above about 50 microns can be used to remove halides from carboxylic acids. Cation-exchange forms of such resins typically have monovalent cations associated with sulfonic functional groups also known as active sites. The active sites are distributed at least over the surfaces of the particle. Preferred resins have a preponderance of their active sites on the external surface of the resin particle. Any monovalent cation, such as Na+ or H+, for which the resin has less affinity than it has for the silver (I) ion, is acceptable. However, the hydrogen form, i.e., H+, is preferred.

Macroreticular resins are distinguished from gelular resins by their physical form. Macroreticular resin particles are comprised of agglomerated microspheres of gelular material fused into a particle having a net-like structure. This structure exhibits macropores within the agglomerated particle. Although the gelular microspheres may shrink in carboxylic acid, as described above, this shrinkage does not affect the macroporous nature of the macroreticular particle. As known to those skilled in the art, the diameter of the pores can be controlled to achieve a particular macroporous structure. Examples of suitable commercially available macroreticular cation-exchange resins include the Amberlyst ® series, which is a product of the Rohm & Haas Company.

The degree or extent of silver exchange is limited only by economic considerations. Loadings of less than about 5% or greater than about 80% typically are inefficient; the former due to the low silver content and thus the shortened useful life and the latter due to the difficulty in obtaining saturation and minor activity improvement which results from the effort. Preferably, between about 10 and 70%, more preferably between about 20 and 60%, and most preferably between about 30 and 50% of the cationic sites should be exchanged with silver(I) ion.

The number of active sites per unit mass or unit volume of resin suitable for use herein may vary over a wide range. The quantity of active sites available on a resin particle is reflected in the property "weight capacity," expressed as milliequivalents per gram (mEq/g). These active sites provide the binding sites for silver ions. The silver ion presence on dry resin preferably exceeds about 0.5 mEq/g, more preferably exceeds about 1.0 mEq/g.

Macroreticular resins are known and have been used previously in the catalysis art. The macroreticular structure allows molecules having diameters larger than the interstices in a gelular structure to come into contact with active sites located on the surface of a pore within the resin particle. Further, macroreticular resins do not depend on the ability of reactants to cause the resin structure to swell in order to afford access to internal active sites. With a macroreticular resin, molecules which do not swell the gel can move through macropores to catalytically-active sites within the particle.

Carboxylic acid contaminated with a halide can be contacted with the silver(I)-exchanged resin in accordance with the method of this invention under a wide range of operating conditions. Generally, a contaminated liquid carboxylic acid stream is contacted with macroreticular resin onto which silver(I) (Ag+) ions have been exchanged under ambient conditions of temperature and pressure. The halide contaminants react with the bound silver to form silver halide. Hydrocarbon moieties associated with the halide esterify the carboxylic acid. For example, in the case of acetic acid contaminated with methyl iodide, methyl acetate would be produced as a byproduct of the iodide removal. Presence in the carboxylic acid stream of this esterification product of reaction typically does not have a deleterious effect on the treated carboxylic acid stream.

The pressure during the contacting treatment is limited only by the physical strength of the resin. For convenience, however, both pressure and temperature are established so that the contaminated carboxylic acid stream is processes as a liquid. Thus, the example, when operating at atmospheric pressure which is generally preferred based on economic considerations, the acceptable temperature range for treatment of acetic acid would be between about 17° C. (acetic acid's freezing point) and about 118° C. (acetic acid's boiling point). Those skilled in the art can determine analogous ranges for other homologous carboxylic acid compounds.

The temperature preferably is kept relatively low to minimize resin degradation. Some cationic macroreticular resins typically begin degrading (via the mechanism of acid-catalyzed aromatic desulfonation) at temperatures of about 150° C. Carboxylic acids having up to about 5 carbon atoms remain liquid at this temperature. Thus, the temperature should be kept below the degradation temperature of the resin utilized. Elevated temperatures also increase the rate of corrosion and the formation of polyvalent metal ion impurities, which as noted earlier can contributed to reduced resin life. Therefore, the operating temperature should be kept as low as possible, consistent with liquid phase operation and the desired kinetics for halide removal. Furthermore, low temperature operation allows less-expensive materials of construction to be used and increases plant safety.

An important feature of the present invention is that acceptable rates of halide removal can be achieved at temperatures lower than temperatures previously required, for example, with prior art gelular resins. These results are illustrated by the comparative examples which follow. For example, when removing methyl iodide from acetic acid, the temperature preferably is below about 60° C., more preferably between about 20° and 50° C., and most preferably between about 25° and 35° C. Temperatures in these ranges minimize resin degradation and corrosion.

It is convenient to express the rate at which the acid stream contacts the exchange resin in terms of a volumetric space velocity (SV), which is defined as the ratio of the volumetric flow per minute of the contaminated acid stream per unit volume of resin (V/Min/V). Acid and resin volumes are expressed in identical units. The rate at which the contaminated acid is contacted with the macroreticular resin is dependent upon the concentration of halide present and the degree of removal desired, the loading of Ag+ on the resin, and the temperature at which the contacting occurs.

At about 25° C. with a methyl iodide impurity concentration of about 20 ppb, space velocities above about 5, i.e., 5 volumes of contaminated acid per minute per volume of resin which is 30–50% silver (I)-exchanged, do not afford efficient removal of iodide from acetic acid. Therefore, under these circumstances, the space velocity preferably is less than about 5, more preferably is between about 0.05 and 2, and most preferably is between about 0.1 and 1.0. As the temperature is raised, however, the maximum space velocity will increase because the activity of the resin increases as temperature increases. The maximum space velocity also increases as the silver ion loading increases. This effect can be seen by comparing Examples 3 and 4 below.

In the known methods for preparing silver exchanged gelular resin, resin is contacted with an aqueous silver nitrate ($AgNO_3$) solution to achieve the silver exchange. However, this technique is less than satisfactory. The reaction is reversible and nitric acid is produced. Nitric acid is both a strong acid and a strong oxidant. The acidity causes the silver ion exchange equilibrium reaction to stop with about 5% of the silver remaining in solution. The oxidizing power of nitric acid requires that the exchanged resin be well-washed before it is used. Also, the supernatant liquid is acidic and contains unreacted silver ions, so an expensive recovery process is required to recover these toxic ions before the stream can be disposed. These inefficient practices highlight the desirability of an improved method for loading silver ions onto a cation exchange resin.

The inventors have discovered that both gelular and macroreticular silver-exchanged resins can be prepared efficiently without the use of silver nitrate by a process which involves reacting silver oxide ($Ag_2O$) with carboxylic acid to yield silver carboxylate. Silver carboxylate is essentially insoluble in carboxylic acids, and only slightly soluble in water. However, when the reaction occurs in the presence of a cation exchange resin, silver ions are exchanged onto the resin almost immediately. Therefore, the insolubility of the silver carboxylate in carboxylic acids does not limit the exchange of silver ions onto the resin. Further, no strong acid is generated as a by-product by this method, so macroreticular resins prepared in this fashion can be used directly to remove halides from carboxylic acids in accordance with the methods described above.

When preparing the silver(I)-exchanged resin, commercially available cation exchange resins should be pre-washed with distilled water to remote any water-soluble acidic material and reducing substances. The acidic material confuses the indirect measurement of exchange through measurement of the increase in acidity as silver replaces hydrogen ions on the resin. Reducing agents lead to the formation of colloidal silver, which remains in the water-acid mixture rather than bonding to the resin. This colloidal silver represents a small economic loss and is a nuisance to remove. Distilled water is used to avoid introduction of undesirable contaminants.

In accordance with the method of the invention, a slurry of resin first is prepared, using an aqueous solution of carboxylic acid. Cation exchange resin products typically are provided in either "wet" (an aqueous slurry of resin particles) or "dry" form. Either form is suitable for use in the method of the present invention, although the "wet" form is advantageously used. If the wet form of a resin is utilized, then water already in the resin preparation must be considered when calculating the amount of water used to prepare the slurry. If the wet form of a resin is used, therefore, less water is added to create resin/carboxylic acid/water slurry. The aqueous solution preferably contains between about 5 and 95 weight percent acid, more preferably between about 25 and 75 weight percent acid, and most preferably between 40 and 60 weight percent acid, with the balance being water. The acid/water ratio is selected to balance the solubility of silver carboxylic (in water) and the rate of silver oxide dissolution, which increases as the concentration of acid increases.

Silver oxide then is added to the resin slurry. The slurry advantageously is maintained at any temperature between the freezing and boiling points of the acid/water solution. A temperature is selected to increase the solubility of silver carboxylate while avoiding localized overheating, which could degrade the resin. The temperature of the slurry preferably is maintained between about 10° and 75° C., more preferably between about 20° and 60° C., and most preferably between about about 25° and 50° C. Temperature control is difficult at higher temperatures; while lower temperatures make it difficult to dissolve the silver carboxylate crust which tends to form on silver oxide particles in the carboxylic acid.

The length of treatment varies inversely with temperature in line with typical reactor kinetics, i.e., lower temperatures require longer treatment times. The upper limit on the length of treatment is essentially an economic consideration, however, because the silver-exchanged resin is very stable. It is seldom necessary to allow treatment to exceed about 3 hours to achieve the desired extent of ion exchange. Attempting to complete the exchange in less than about 20 minutes, however, requires relatively high temperatures and makes temperature control (i.e., avoidance of localized overheating) difficult. Therefore, the length of treatment preferably is between about 20 minutes and 3 hours, more preferably between 30 minutes and 2 hours.

Any water-soluble carboxylic acid, except formic acid, can be utilized in this process. Formic acid is unacceptable because it reduces silver(I) ions to metallic silver. Acetic acid is preferred because it lacks the unpleasant odor, toxicity, and high cost of the higher molecular weight homologs. Also, the lower molecular weight of acetic acid provides a greater concentration of carboxylic acid moieties per unit mass of acid. It is especially preferred to utilize pure carboxylic acid of the type which subsequently will be treated by contacting it with the treated resin, as no additional compounds then are introduced into the treated carboxylic acid stream.

After the exchange reaction has progressed to the desired extent, the resin is separated from the solution, and can be used directly without rinsing as was required when using silver nitrate as the silver source. While both water and carboxylic acid remain in the resin pores and on the surface of the resin particles, these components will be displaced by carboxylic acid during the halide-removal process. The presence of water or a homologous carboxylic acid affects neither the halide-removal process nor the subsequent esterification reaction. Recycled acid in the unsaturated ester process contains significantly more water than a typical resin charge can hold. Therefore, the small additional amount of water displaced from the resin as described herein is insignificant in the esterification system.

Those skilled in the art recognize that the method of resin preparation described herein can be used to prepare silver-exchanged gelular resin in addition to macroreticular resin simply by using gelular resin as the starting material. Gelular resin will not shrink during preparation as it does during contact with contaminated carboxylic acid because preparation is carried out in aqueous solution, which protects gelular resin on shrinkage. However, in the above-described method of halide removal, macroreticular resin is preferred.

The following examples serve to further illustrate the invention.

EXAMPLES 1-6

In the following examples, a silver-exchanged resin bed was prepared in the following manner. Referring to FIG. 2, a small plug of glass wool 10 was placed at the bottom of a 100 mL jacketed burette 11 having an internal diameter of about 1.5 centimeters and containing 60 mL of distilled water. A small amount of sand was poured through the water to form a level bed 12. Any sand remaining on the side of the burette was rinsed down with distilled water and the water was drained down to 60 mL. A quantity of selected resin 13, mixed with water to form a slurry, was poured into the burette with a funnel. The resin was rinsed with distilled water while water was drained to maintain approximately 60 mL volume in the burette. The burette was tapped lightly to form an even bed of resin. The temperature of the system was maintained by circulating constant temperature water through jacket 14 of the burette.

The resin was rinsed in the column with about 10 bed volumes of glacial acetic acid to remove most of the water. A graduated funnel 19 with a metering stopcock 20 was used to regulate the flow of glacial acetic acid contaminated with 20 ppb methyl iodide to the column. The rate of introduction of contaminated acid was adjusted to maintain level of acid over the resin constant, thereby ensuring constant flow. Methyl iodide in the acid was measured by a gas chromatographic method with an electron-capture detector.

Contaminated acid flowed through resin bed 13 and iodide was removed by the resin. Treated acid flowed through tube 15 to sample point 16. Loop 17 was used to prevent accidental draining of the column. The loop also has a minor effect on the liquid head in the resin column. Vent 18 prevented syphoning.

Resin beds utilized in these example were prepared in various bed depths, described as "long" and "short" beds. A "short" bed was up to about 50 percent as deep as a "long" bed. "Long" beds were between about 20 and 30 cm deep. Precise bed depths are described in the Tables.

COMPARATIVE EXAMPLE 1

A prior art method of preparing silver(I)-exchanged resin was utilized to prepare a 52% exchanged Dowex ® 50W-X8 gelular resin, 20-50 mesh. Dowex ® is a registered trademark of Dow Chemical Company, and Dowex 50W-X8 is equivalent to Rohm & Haas Amberlite ® IR-120, which was used by Hingorani et al. The resin first was rinsed with a small amount of distilled water to remove color and acidity. Fifty grams of resin in a 250 mL beaker was treated with 0.1 or 0.5N aqueous silver nitrate solution sufficient to provide the desired amount of silver and to cover the resin. The slurry was stirred and then the beaker was covered and allowed to stand at room temperature (20° C.) for an hour. The slurry was then filtered to remove excess silver nitrate solution without allowing the resin to dry. The resin was washed with several portions of distilled water until the pH of the filtrate was equal to or greater than six. Damp exchanged resins were stored in tightly-sealed brown bottles at room temperature.

Glacial acetic acid contaminated with 20 ppb methyl iodide then was passed through a fixed bed of this resin at 60° C. in various trials wherein space velocity was varied. The gel contracted during the trial. Results showing the concentrations of methyl iodide remaining in the treated acetic acid are tabulated below.

TABLE 1

| Trial | Space Velocity, V/Min/V | Outlet Methyl Iodide Concentration, ppb |
|---|---|---|
| 1A | 0.12 | 0.16 |
| 1B | 0.28 | 0.58 |
| 1C | 0.58 | 3.06 |

TABLE 1-continued

| Trial | Space Velocity, V/Min/V | Outlet Methyl Iodide Concentration, ppb |
|---|---|---|
| 1D | 0.89 | 6.56 |
| 1E | 1.13 | 10.41 |
| 1F | 1.37 | 11.49 |
| 1G | 1.54 | 13.14 |
| 1H | 1.73 | 13.08 |

COMPARATIVE EXAMPLE 2

The method of Example 1 was repeated at a bed temperature of 40° C. utilizing 100% exchanged (2.9 mEqs/mL) gelular resin prepared in accordance with the preparation described in Example 1.

TABLE 2

| Trial | Space Velocity, V/Min/V | Outlet Methyl Iodide Concentration, ppb |
|---|---|---|
| 2A | 0.05 | 0.76 |
| 2B | 0.092 | 1.37 |
| 2C | 0.150 | 3.67 |
| 2D | 0.151 | 2.26 |
| 2E | 0.315 | 4.75 |
| 2F | 0.630 | 10.14 |

EXAMPLE 3

Macroreticular resin Amberlyst ® 15 was 10% silver-exchanged. This exchanged resin was prepared in accordance with the prior art method described in Example 1 and a long bed was prepared. The technique of the invention described in Example 1 was used to remove methyl iodide from acetic acid. These trials were run at about 20° C.

TABLE 3

| Trial | Space Velocity, V/Min/V | Outlet Methyl Iodide Concentration, ppb |
|---|---|---|
| 3A | 0.02 | 0.10 |
| 3B | 0.06 | 0.08 |
| 3C | 0.11 | 0.18 |
| 3D | 0.14 | 0.26 |
| 3E | 0.18 | 0.54 |
| 3F | 0.31 | 2.48 |
| 3G | 0.39 | 3.25 |
| 3H | 0.50 | 5.32 |
| 3I | 0.61 | 7.52 |

EXAMPLE 4

Example 3 was repeated with an 49% Amberlyst ® 15 silver(I)-exchanged macroreticular resin. The results are summarized below.

TABLE 4A

| "Long" Bed Bed depth 28.7 cm | | |
|---|---|---|
| Trial | Space Velocity, V/Min/V | Outlet Methyl Iodide Concentration, ppb |
| 4A | 0.083 | 0.12 |
| 4B | 0.127 | 0.10 |
| 4C | 0.185 | 0.10 |
| 4D | 0.240 | 0.09 |
| 4E | 0.290 | 0.08 |
| 4F | 0.360 | 0.11 |
| 4G | 0.474 | 0.13 |
| 4H | 0.57 | 0.11 |

TABLE 4B

"Short" Bed
Bed depth 6.7 cm

| Trial | Space Velocity, V/Min/V | Outlet Methyl Iodide Concentration, ppb |
|---|---|---|
| 4I | 0.56 | 0.16 |
| 4J | 1.26 | 0.58 |
| 4K | 1.88 | 1.50 |
| 4L | 2.57 | 2.69 |
| 4M | 2.96 | 3.61 |

EXAMPLE 5

Amberlite ® 200 macroreticular resin, which was 46% (0.87 mEq/mL) silver-exchanged utilizing the known silver nitrate technique, was used in the method described in Example 1 to yield the following results:

TABLE 5A

"Long" Bed
Bed depth 22.2 cm

| Trial | Space Velocity, V/Min/V | Outlet Methyl Iodide Concentration, ppb |
|---|---|---|
| 5A | 0.19 | 0.26 |
| 5B | 0.22 | 0.19 |
| 5C | 0.37 | 0.20 |
| 5D | 0.39 | 0.15 |
| 5E | 0.94 | 0.51 |
| 5F | 1.02 | 0.53 |

TABLE 5B

"Short" Bed
Bed depth 8.8 cm

| Trial | Space Velocity, V/Min/V | Outlet Methyl Iodide Concentration, ppb |
|---|---|---|
| 5G | 0.83 | 0.38 |
| 5H | 1.50 | 1.27 |
| 5I | 2.26 | 3.38 |
| 5J | 3.18 | 5.14 |
| 5K | 4.09 | 7.59 |

EXAMPLE 6

Amberlyst XN-1010 ® macroretular resin having 71% silver(I)-exchanged (1.17 mEq/mL) was used as in Example 5, and yielded the following results:

TABLE 6A

"Long" Bed
Bed depth 24.2 cm

| Trial | Space Velocity, V/Min/V | Outlet Methyl Iodide Concentration, ppb |
|---|---|---|
| 6A | 0.024 | 0.37 |
| 6B | 0.079 | 0.33 |
| 6C | 0.146 | 0.34 |
| 6D | 0.223 | 0.43 |
| 6E | 0.290 | 0.38 |
| 6F | 0.308 | 0.36 |
| 6G | 0.357 | 0.68 |
| 6H | 0.367 | 0.96 |
| 6I | 0.397 | 0.90 |
| 6J | 0.439 | 1.25 |
| 6K | 0.508 | 2.08 |

TABLE 6B

"Short" Bed
Bed depth 6.3 cm

| Trial | Space Velocity, V/Min/V | Outlet Methyl Iodide Concentration, ppb |
|---|---|---|
| 6L | 0.70 | 4.08 |
| 6M | 0.92 | 5.46 |
| 6N | 1.23 | 8.20 |
| 6P | 1.27 | 8.41 |
| 6Q | 1.94 | 10.52 |
| 6R | 2.00 | 10.20 |
| 6S | 2.59 | 11.29 |
| 6T | 2.74 | 11.24 |
| 6U | 3.02 | 12.79 |
| 6V | 3.09 | 12.38 |
| 6W | 3.4 | 12.59 |

These examples illustrate the clear superiority of macroreticular resins (Examples 3-6) over gelular resins (Examples 1,2) when used in the method of the invention to remove halide impurity. The examples also illustrate the preferred nature of Amberlyst 15 and 200 (Examples 3, 4 and 5) over the other macroreticular resin (Example 6). These preferred resins have a preponderance of active sites on the external surface of the particles. Comparison of "long" and "short" beds illustrated that each is effective at halide removal.

EXAMPLE 7

40 mL of wet Amberlite ® 200 in the H+ form was rinsed with 300 mL of distilled water. The filtrate had a pH of 6. The resin was dried with a stream of air to 31.35 g (44 mL). The resin was then treated with 100 mL of 0.5N aqueous silver nitrate solution (50 mEq) in a 250-mL beaker. The slurry was allowed to stand at room temperature for two hours with occasional swirling. The slurry was filtered and washed with three 100 mL portions of distilled water until the pH rose to 6. The combined filtrated were treated with sodium chloride and turned cloudy due to precipitated silver chloride. The mixture was then titrated with 0.5N sodium hydroxide solution to determine the equivalents of hydrogen ion exchanged by silver. Only 70% of the silver, 34.75 mEq, was incorporated into the resin even though that was only half of the capacity of the resin. This silver-exchanged resin was utilized in Example 5.

EXAMPLE 8

Finely divided silver oxide (2.60 g, 24.1 mEq.) was add to a solution of 250 grams of acetic acid in 250 grams of distilled water with stirring. Little reaction took place in an hour at room temperature. The mixture was heated slowly to 50° C. with stirring. After one hour (at 33° C.) the solution had already become clear and colorless. The mixture was allowed to stand at room temperature and some colorless needless of silver acetate precipitated.

The mixture was heated with gentle stirring to 50° C. to dissolve the silver acetate. Wet Amberlite ® 200 in the H+ form (17.6 g) was added to the mixture. The mixture was stirred for three hours at 50° C. and then allowed to cool to room temperature without stirring. The mixture was filtered and filtrate was treated with 25 mL of 0.4N sodium chloride solution. The hazy mixture was allowed to settle and was then filtered to recover a film of precipitate beneath a clear solution. The precipitate (silver chloride) was washed with water and dried at 120° C. Only 0.13% of the original silver (0.0046 g, 0.032 mEq. of AgCl) was not exchanged onto the resin.

EXAMPLE 9

Distilled water (2500 pounds) was charged to a 500-gallon glass-lined double cone blender. Amberlyst ® 15 wet form resin (2177 pounds) was charged to the vessel. The mixture was rotated at 2 rpm for fifteen minutes. The water was then drawn off. Another 2500 pounds of distilled water was charged, and the wash was repeated. Silver oxide powder (182.4 pounds) was charged. Distilled water (770 pounds), enough to just cover the solids, was charged. The mixture was rotated for an hour to thoroughly mix the reactants. Acetic acid (1310 pounds) was pumped in. The mixture was heated to 50° C. and held there for three hours while being rotated. A mixture of about 40% acetic acid in water (2211 pounds) was drained from the resin. The resin was dried under vacuum at 50° C. while being rotated for ten hours so that 1900 pounds of resin was obtained. The acetic acid solution drained from the resin had less than 100 ppb Ag+.

Examples 7-9 illustrated the superior efficiency of silver ion utilization achieved by the method of the invention.

Although preferred embodiments of this invention have been discussed herein, those skilled in the art will appreciate that changes and modifications may be made without departing from the spirit of this invention, as defined in and limited only by the scope of the appended claims.

I claim:

1. A method of preparing a silver(I)-exchanged resin comprising;
   (a) preparing a slurry of a cation exchange resin in aqueous carboxylic acid solution;
   (b) adding silver oxide to the slurry to form silver(I) carboxylate and to bind silver(I) ions of said silver (I) carboxylate onto active sites of said resin by ion exchange; and
   (c) recovering silver(I)-exchanged resin from said slurry.

2. The method of claim 1 wherein the cation exchange resin of step (a) is a macroreticular resin.

3. The method of claim 1 wherein the aqueous carboxylic acid solution of step (a) comprises between about 25 and 75 weight percent acid.

4. The method of claim 3 wherein the aqueous carboxylic acid solution of step (a) comprises between about 40 and 60 weight percent acid.

5. The method of claim 1 wherein the temperature of the slurry of step (a) is maintained between about 20° and 60° C.

6. The method of claim 1 wherein the carboxylic acid of step (a) has between 2 and 5 carbon atoms.

7. The method of claim 6 wherein the carboxylic acid of step (a) is acetic acid.

8. The method of claim 7 wherein the cation exchange resin of step (a) is a macroreticular resin.

9. The method of claim 1 wherein the silver(I) ions are bound onto at least about 10 percent of the active sites.

10. The method of claim 1 wherein the silver(I) ions bound onto the active sites have a weight capacity of at least about 0.5 mEq per gram of dry, silver(I)-exchanged resin.

11. The method of claim 1 wherein the resin of step (a) comprises a macroreticular polystyrene resin crosslinked with divinylbenzene.

12. The method of claim 1 wherein the resin of step (a) comprises a sulfonated macroreticular polystyrene resin crosslinked with divinylbenzene.

13. The method of claim 12 wherein the silver(I) ions are bound onto at least about 10 percent of the active sites.

* * * * *